United States Patent [19]

Nishida et al.

[11] Patent Number: 5,675,090

[45] Date of Patent: Oct. 7, 1997

[54] METHOD FOR MEASURING THE AMOUNT OF AN ACTIVE CLAYEY COMPONENT CONTAINED IN MOLDING GREENSAND

[75] Inventors: Tadashi Nishida; Kazuharu Matsui, both of Toyokawa, Japan

[73] Assignee: Sintokogio, Ltd., Japan

[21] Appl. No.: 631,412

[22] Filed: Apr. 12, 1996

[30] Foreign Application Priority Data

Apr. 14, 1995 [JP] Japan ................................. 7-113630

[51] Int. Cl.$^6$ ................................................. G01N 11/00
[52] U.S. Cl. ................................................. 73/823; 73/866
[58] Field of Search ............................. 73/866, 821, 818, 73/823

[56] References Cited

U.S. PATENT DOCUMENTS 4,930,354  6/1990  Knopp et al. ........................... 73/823

*Primary Examiner*—Robert Raevis
*Attorney, Agent, or Firm*—Limbach & Limbach L.L.P.

[57] ABSTRACT

A method is disclosed to accurately and easily measure the amount of an active clayey component contained in molding greensand. A test piece is produced by feeding a predetermined amount of the molding greensand into a testing receptacle. The test piece is then tested to obtain its compressive strength. The amount of the active clayey component contained in it is determined from the measured compressive strength by using previously obtained data on the relation between the compressive strength and the active clayey component of molding greensand which is used on a mold-producing line or at a factory.

1 Claim, 3 Drawing Sheets

5,675,090

METHOD FOR MEASURING THE AMOUNT OF AN ACTIVE CLAYEY COMPONENT CONTAINED IN MOLDING GREENSAND

FIELD OF THE INVENTION

This invention relates to a method which is suitable for measuring the amount of the active clayey component contained in molding greensand.

DESCRIPTION OF THE PRIOR ART

Generally, the coloring-matter-adsorbing method has been used as one that can measure with great accuracy and sensitivity the amount of an active clayey component contained in molding greensand. This method is based on the idea that the amount of the active clayey component contained in molding greensand is proportional to its ability to adsorb coloring matter. In this method 0.7 g/l (770 ppm) of Methylene Blue is used as coloring matter. It is added to sand at the rate of 3 cc of Methylene Blue per 1–2 g sand, to produce a total solution of 300 cc, wherein the Methylene Blue is absorbed by the sand under a constant temperature. The clayey component is separated from the sand, and the absorbance of the Methylene Blue by the clayey component is then measured by using a beam having a 610 mμ wavelength, and its concentration (value in mg) is determined by a working curve for a standard solution.

However, by this method coloring matter cannot be easily measured at factories or other places where cast products are manufactured.

Further, recently thin cast products of accurate sizes have been required. Therefore continuously providing many greensand molds, each of which has a cavity of which the size is accurate, is required. To do so, a necessary amount of bentonite must be supplied to the greensand. This amount of bentonite is determined depending on the amount of the active clayey component in the greensand.

SUMMARY OF THE INVENTION

This invention is made in view of the facts mentioned above, and aims to provide a method for accurately, easily, and definitely determining the amount of the active clayey component in molding greensand.

To this end, the method of the present invention for measuring the amount of the active clayey component contained in molding greensand is characterized in that it comprises the steps of manufacturing a test piece by feeding a predetermined amount of molding greensand of a mold-producing line or factory into a testing receptacle having predetermined dimensions and compressing the greensand in the testing receptacle, measuring the compressive strength of the test piece, and determining the amount of the active clayey component in the greensand according to previously obtained data on the relation between the compressive strength and the amount of the active clayey component of molding greensand of the mold-producing line or factory.

As a result of the inventors' keen study of molding greensand, it was found that the compressive strength of test pieces of greensand differs due to the water content of the test pieces of the greensand when they are produced by the method of JIS (Japanese Industrial Standard) Z-2601 for producing a test piece for compressive strength (three-time-ramming-type method), and that, when test pieces are produced by compressing or squeezing greensand as in the present invention, the compressive strength of all the test pieces is substantially constant even if the compactability values and/or water content of the test pieces of molding greensand differ.

Further, it was also found that whether the test pieces are manufactured by the compressing method of the present invention or by JIS Z 2601, the compressive strength of the test pieces and their clayey components have, in both cases, a similar proportional relation.

DESCRIPTION OF THE PREFERRED EMBODIMENT

The embodiment of the present invention will now be explained by reference to FIGS. 1, 2, and 3.

First, to make a test piece of molding greensand to determine the amount of its active clayey component by a method similar to the three-time-ramming method of JIS Z 2601, a cylindrical testing receptacle having a cavity with an inner diameter of 50 mm and 100 mm high is placed on a flat plate. Greensand, which is used on a line or at a factory to produce molds, is charged into the cavity and compressed under a set force (100–400 kgf) by a press plate which is inserted from the upper opening of the cylindrical testing receptacle into its cavity. The produced test piece is set on a compressive-strength testing machine to obtain its compressive strength. The amount of its active clayey component is then determined by using the data on the obtained compressive strength and previously obtained data on the relation between the compressive strength and the clayey component of molding greensand of the mold-producing line or factory. (The relation is explained below by reference to FIG. 3.)

Some molding greensand having different compactabilities was produced by adding different volumes of water to sand, and test pieces having different compactabilities were produced by using the molding greensand by both the three-time-ramming-type method and the compressing method of the present invention. The compressive strengths of these test pieces were then measured. The test results are shown in FIG. 1.

Figure 1:
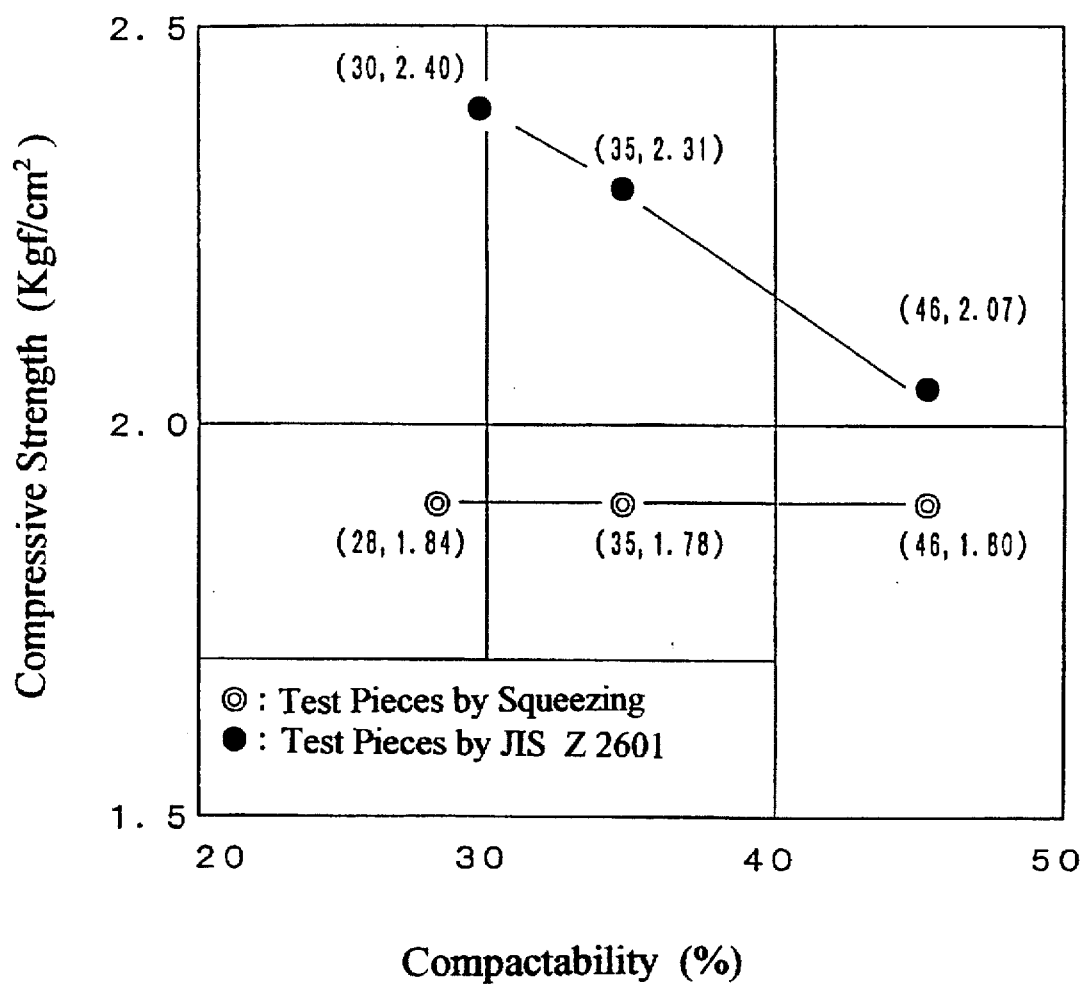
FIG. 1 is a graph of the measured compressive strength of test pieces which are made of greensand having different water contents and therefore different compactabilities, and which are produced by both the pressing method of the present invention and JIS Z 2601.

As will be seen from FIG. 1, the compressive strength of the test pieces that are produced by JIS Z 2601 (shown by black circles) varies depending on the variation in the compactability of the greensand. However, the compressive strength of the test pieces that are produced by the compressing method of the present invention (shown by double circles) is almost constant when the compactability of the greensand varies, but is in the range of between 28 and 46%, in which the greensand is used for molding greensand.

Some molding greensand having different water contents was produced by adding different volumes of water to sand.

and test pieces having different water contents were produced using the molding greensand by both the three-time-ramming-type method and the compressing method of the present invention. The compressive strengths of these test pieces were then measured. The test results are shown in FIG. 2.

Figure 2:
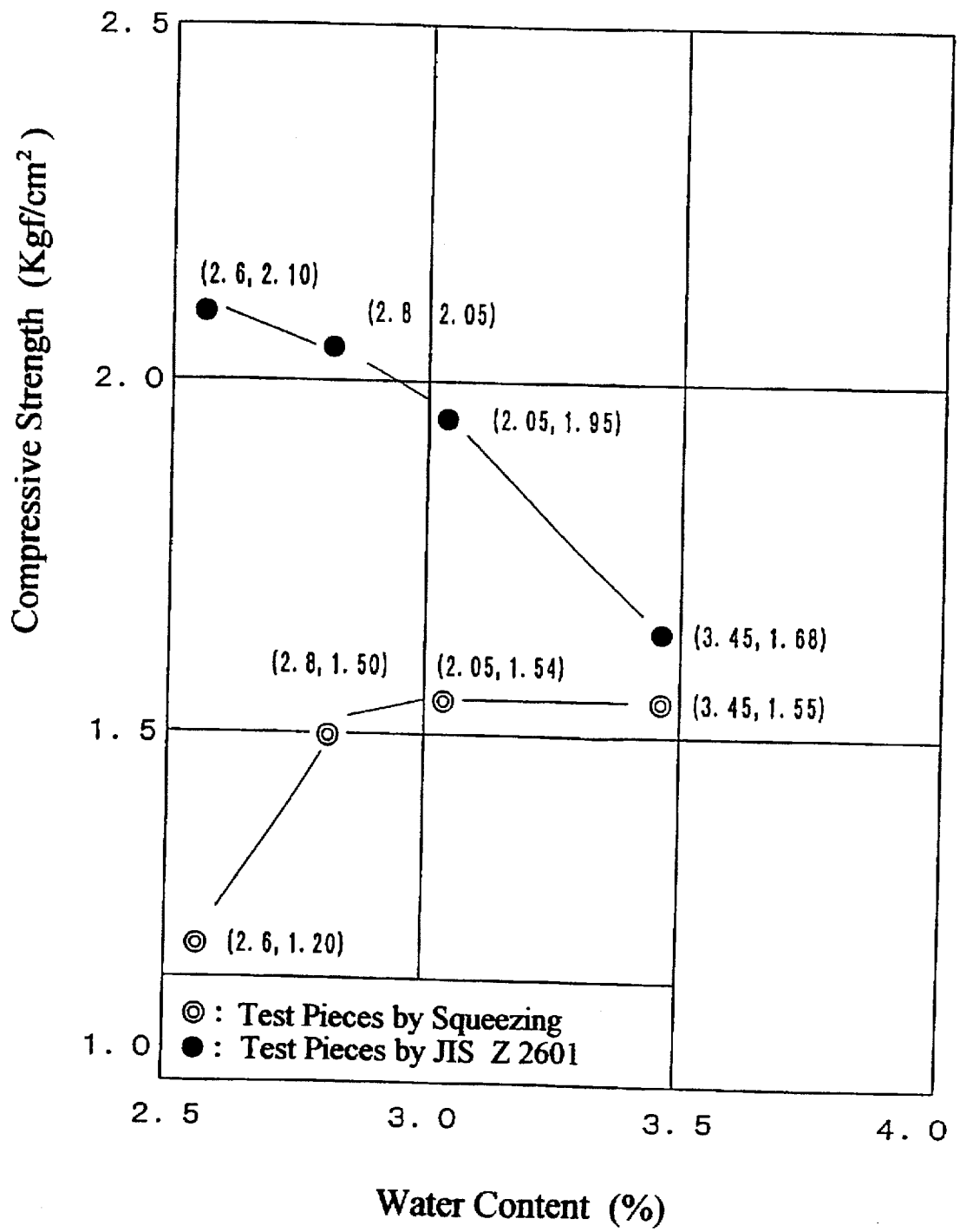
FIG. 2 is a graph of the measured compressive strength of test pieces which are made of greensand having different water contents, and which are produced as are the test pieces of FIG. 1.

As will be seen from FIG. 2, the compressive strength of the test pieces that are produced by JIS Z 2601 (shown by black circles) varies depending on the water content of the greensand. However, the compressive strength of the test pieces that are produced by the compressing method of the present invention (shown by double circles) is almost constant even when the water content of the greensand varies, but it is within a range (between 2.8 and 3.45%) in which the greensand can be used for molding greensand.

Some molding greensand having different active clayey components was produced by adding different volumes of water and bentonite to sand, and test pieces having different amounts of active clayey components were produced with the molding greensand by both the three-time-ramming-type method and the compressing method of the present invention in the same way as in FIG. 1. The compressive strengths of these test pieces were then measured. The test results are shown in FIG. 3. The amounts of the active clayey components were measured by the coloring-matter-adsorption method.

Figure 3:
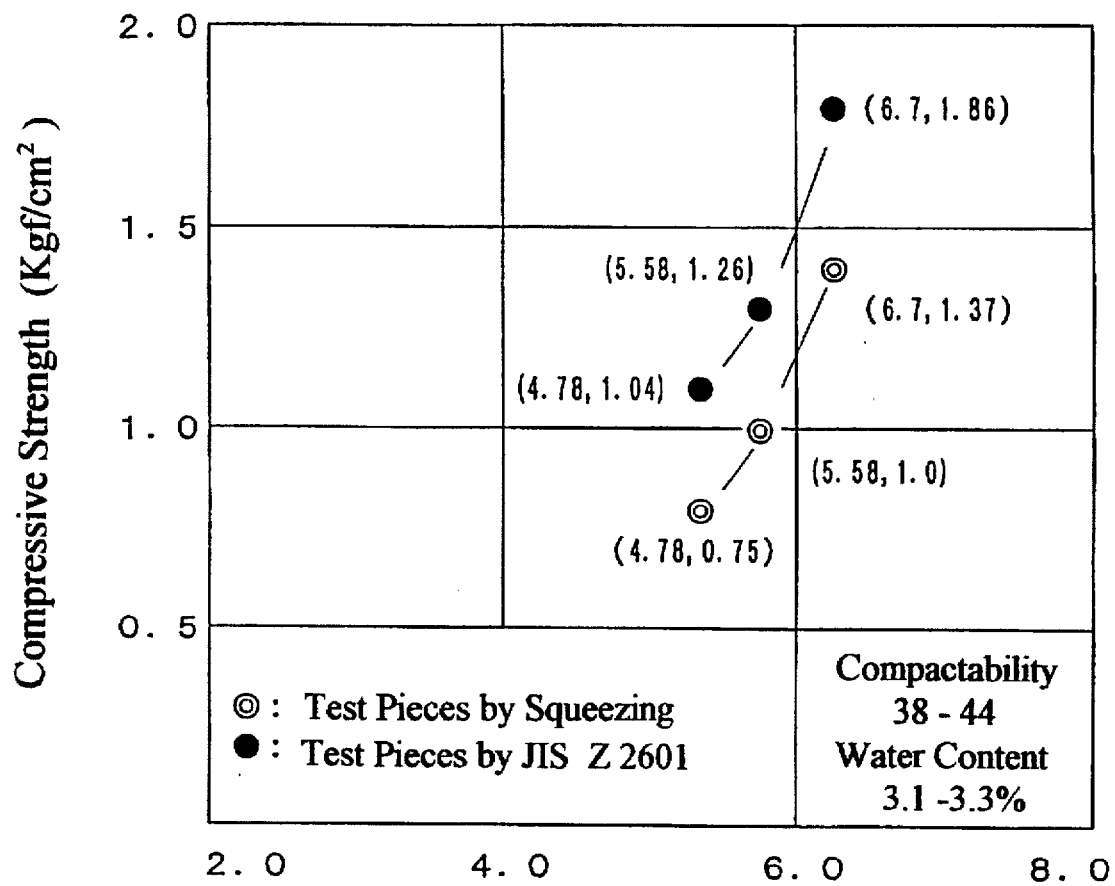
FIG. 3 is a graph of the measured compressive strength of test pieces which are made of greensand having different water and bentonite contents, and which are produced both by the pressing method of the present invention and JIS Z 2601, as are those of FIG. 1.

FIG. 3 shows that the compressive strength of the test pieces that are produced by JIS Z 2601 (shown by black circles) is approximately proportional to the amount of the active clayey component in the same relation that the compressive strength of the test pieces that are produced by the compressing method of the present invention (shown by double circles) is approximately proportional to the amount of the active clayey component. Although the amount of the active clayey component is greater in the test pieces produced by JIS Z 2601 than in those produced by the compressing method of the present invention, FIG. 3 shows that the amount of the active clayey component can be determined from the compressive strength in a one-to-one relation for the test pieces produced by either JIS Z 2601 or by the compressing method of the present invention.

As is clear from the preceding description, since the method of the present invention includes the steps of manufacturing a test piece by feeding a predetermined amount of molding greensand into a testing receptacle having predetermined dimensions and compressing the greensand in the testing receptacle, measuring the compressive strength of the test piece, and determining the amount of an active clayey component contained in the greensand from the measured compressive strength by using previously obtained data on the relation between the compressive strength and the active clayey component of molding greensand which is used on a mold-producing line or at a factory, and since therefore the compressive strength of the test piece is not affected by the compactability and/or water content of the greensand, the method enables an active clayey component contained in molding greensand to be accurately, easily, and definitely obtained, compared to the conventional method.

What we claim is:

1. A method for measuring the amount of an active clayey component contained in molding greensand, comprising the steps of:

adjusting molding greensand of a mold-producing line or factory such that the molding greensand can be shaped in a mold;

manufacturing a test piece by feeding a predetermined amount of the adjusted molding greensand into a testing receptacle having predetermined dimensions;

compressing the greensand in the testing receptacle;

measuring the compressive strength of the test piece; and determining the amount of the active clayey component contained in the greensand from the measured compressive strength by using previously obtained data on a relation between the compressive strength and the amount of the active clayey component of molding greensand of the mold-producing line or factory, wherein, in the adjusting step, the greensand is adjusted to have a compactibility in the range of 20 to 46% and a water content in the range 2.8 to 3.45%.

* * * * *